United States Patent
De Heij et al.

(10) Patent No.: US 9,546,944 B2
(45) Date of Patent: Jan. 17, 2017

(54) NEPHELOMETRIC PROCESS TURBIDIMETER

(71) Applicant: HACH LANGE GMBH, Berlin (DE)

(72) Inventors: Bas De Heij, Dormagen (DE); Perry Palumbo, Fort Collins, CO (US)

(73) Assignee: HACH LANGE GMBH, Berlin (DE)

(*) Notice: Subject to any disclaimer, the term of this patent is extended or adjusted under 35 U.S.C. 154(b) by 0 days.

(21) Appl. No.: 14/951,501

(22) Filed: Nov. 25, 2015

(65) Prior Publication Data

US 2016/0153886 A1 Jun. 2, 2016

(30) Foreign Application Priority Data

Nov. 27, 2014 (EP) .................................... 14195057

(51) Int. Cl.
*G01N 21/00* (2006.01)
*G01N 15/14* (2006.01)
*G01N 21/05* (2006.01)
*G01N 21/53* (2006.01)
*G01N 33/18* (2006.01)

(52) U.S. Cl.
CPC ...... *G01N 15/1404* (2013.01); *G01N 15/1436* (2013.01); *G01N 21/05* (2013.01); *G01N 21/53* (2013.01); *G01N 33/18* (2013.01); *G01N 2201/0642* (2013.01)

(58) Field of Classification Search
CPC ........ G01N 21/47; G01N 21/49; G01N 21/05; G01N 21/532; G01N 21/4785; G01N 21/53; G01N 21/15; G01N 21/0303; G01N 21/51; G01N 2021/513; G01N 2021/4726; G01N 15/1404; G01N 2201/068; G01N 2201/064; G01N 2201/0227

USPC ......... 356/246, 335–343, 432–440; 422/512, 422/546, 550, 560

See application file for complete search history.

(56) References Cited

U.S. PATENT DOCUMENTS

| | | | |
|---|---|---|---|
| 5,446,544 A | 8/1995 | Beers | |
| 5,574,232 A | 11/1996 | Davidson et al. | |
| 7,046,347 B1 * | 5/2006 | Amend | G01N 21/51 356/338 |
| 7,659,980 B1 * | 2/2010 | Mitchell | G01N 21/4785 356/338 |
| 2010/0077874 A1 | 4/2010 | Kanomata | |

(Continued)

FOREIGN PATENT DOCUMENTS

| | | |
|---|---|---|
| DE | 30 27 317 A1 | 2/1982 |
| EP | 2 168 647 A1 | 3/2010 |
| WO | WO 88/02855 A1 | 4/1988 |

*Primary Examiner* — Hoa Pham
(74) *Attorney, Agent, or Firm* — Norman B. Thot

(57) ABSTRACT

A nephelometric process turbidimeter for measuring a turbidity of a liquid sample includes a transparent sample vial which comprises a sample vial lateral inner surface. A vial head comprises a vial head lateral inner surface. The vial head and the sample vial together define a sample volume of a liquid sample having a shape of a cylinder. A sample inlet opening is arranged at the vial head and comprises an inlet opening axis. A sample outlet opening is arranged at the cylindrical vial head lateral inner surface to be axially closer to the sample vial than to the sample outlet opening. The inlet opening axis is inclined with respect to an inlet cross plane with an inclination angle of 10° to 80°, and is angled with respect to a radius line from a middle of the cylinder to the sample inlet opening with a tangency angle of more than 15°.

9 Claims, 3 Drawing Sheets

(56) References Cited

U.S. PATENT DOCUMENTS

2016/0153891 A1* 6/2016 Battefeld ............... G01N 21/51
                                                    356/246
2016/0153893 A1* 6/2016 Battefeld ............... G01N 21/51
                                                    356/246
2016/0231240 A1* 8/2016 Battefeld ............... G01N 21/51

* cited by examiner

NEPHELOMETRIC PROCESS TURBIDIMETER

CROSS REFERENCE TO PRIOR APPLICATIONS

Priority is claimed to European Patent Application No. EP 14195057.6, filed Nov. 27, 2014. The entire disclosure of said application is incorporated by reference herein.

FIELD

The present invention relates to a nephelometric process turbidimeter to continuously or quasi-continuously measure the turbidity of a liquid sample, for example, drinking water, in a transparent sample vial.

BACKGROUND

A nephelometric turbidimeter determines the concentration of solid particles suspended in a liquid sample within a sample vial by projecting a measurement light beam into the liquid sample within the vial. An optical turbidity sensor which is provided outside the cuvette body detects the amount of light scattered by the suspended solid particles at an angle of, typically, 90° with respect to the light beam axis. In a process turbidimeter, the liquid sample within the sample volume defined by the sample vial is exchanged continuously, quasi-continuously, or periodically to continuously supply a control circuit with turbidity values for controlling the turbidity of the liquid. The measurement frequency or response time of the turbidimeter is defined by the sample exchange time, which is the time needed to completely exchange the sample within the vial in a defined grade as, for example, by 99%. The higher the measurement frequency of the turbidimeter is, the shorter is the reaction time of the control circuit, and the shorter the reaction time of the control circuit is, the better is the control quality of the control circuit.

In a state of the art nephelometric process turbidimeter, a separate vial head is provided on the vial opening to thereby define, together with the sample vial, a closed sample volume. The vial head is provided with a sample inlet opening and a sample outlet opening, both being located at the end wall of the vial head, the end wall lying in a cross plane with respect to the longitudinal axis of the cylindrical sample vial. The sample exchange time of this arrangement ranges from 30 to 120 seconds.

SUMMARY

An aspect of the present invention is to provide a nephelometric process turbidimeter to measure the turbidity of a liquid sample which has a decreased sample exchange time.

In an embodiment, the present invention provides a nephelometric process turbidimeter for measuring a turbidity of a liquid sample which includes a sample vial configured to be transparent. The sample vial comprises a cylindrical sample vial lateral inner surface. A vial head comprises a cylindrical vial head lateral inner surface. The vial head and the sample vial together define a sample volume of a liquid sample having a shape of a cylinder. A sample inlet opening comprises an inlet opening axis. The sample inlet opening is arranged at the vial head and is configured to have the liquid sample flow therethrough into the sample volume. A sample outlet opening is arranged at the cylindrical vial head lateral inner surface of the vial head to be axially closer to the sample vial than to the sample outlet opening. The sample outlet opening is configured to have the liquid sample flow therethrough out of the sample volume. The inlet opening axis of the sample inlet opening is inclined with respect to a plane cutting across the sample inlet opening with an inclination angle of 10° to 80°, and is angled with respect to a radius line from a middle of the cylinder to the sample inlet opening with a tangency angle of more than 15°.

BRIEF DESCRIPTION OF THE DRAWINGS

The present invention is described in greater detail below on the basis of embodiments and of the drawings in which.

DETAILED DESCRIPTION

Figure 1:
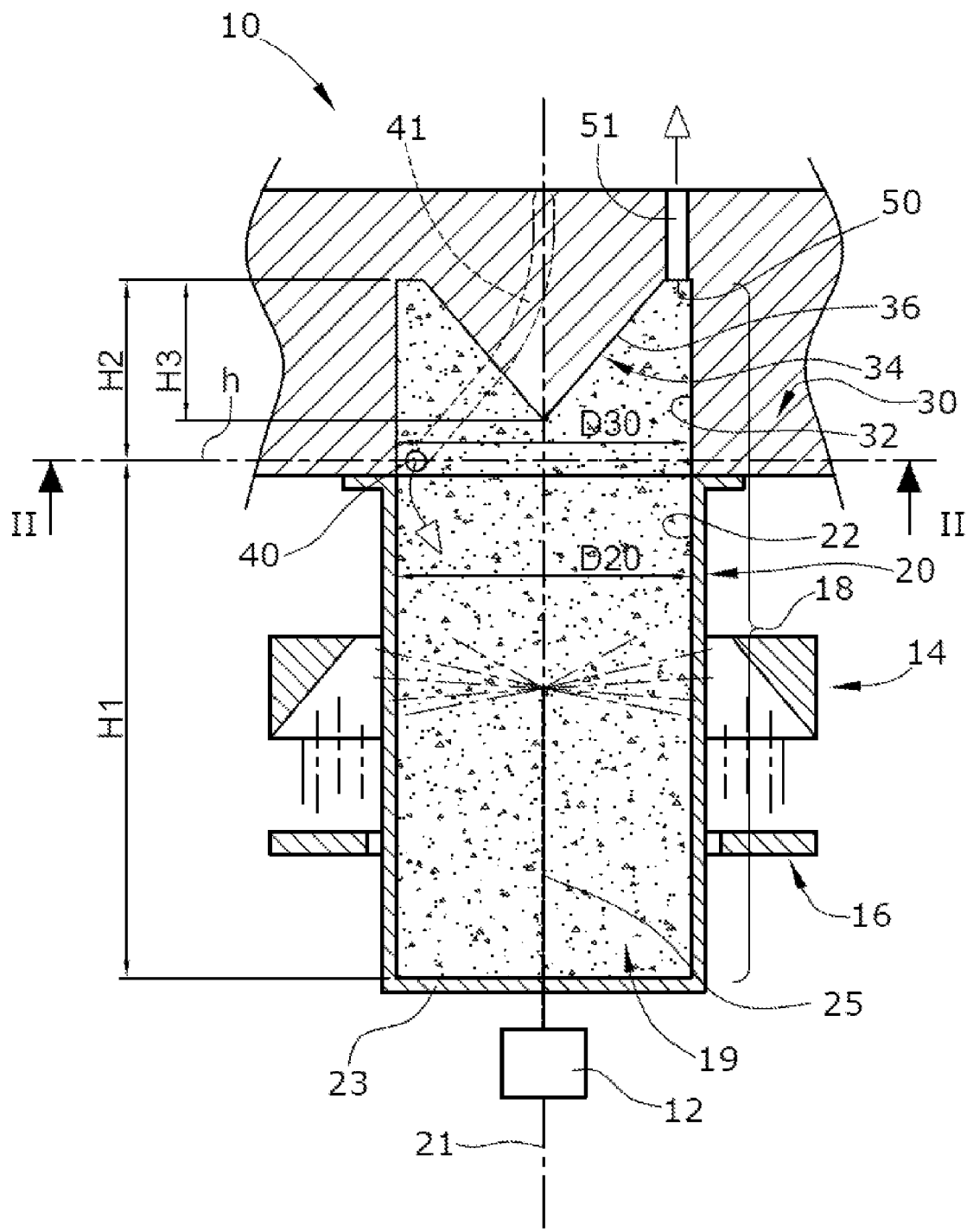
FIG. 1 shows a process turbidimeter with a sample volume defined by a sample vial and a vial head with a sample inlet opening and a sample outlet opening provided at the vial head.
Figure 2:
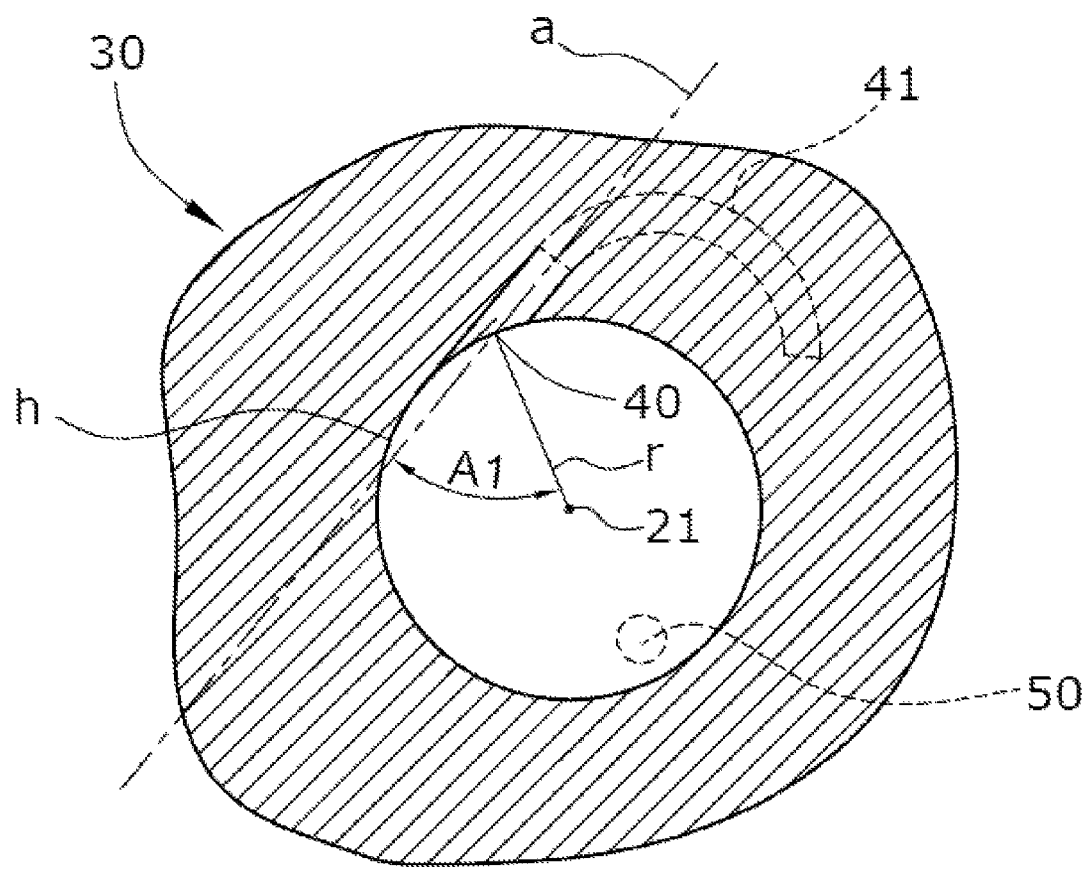
FIG. 2 shows a cross section of the inlet opening plane II-II of FIG. 1.

The transparent sample vial and the separate vial head both define the sample volume for the liquid sample. The lateral inner surface of the sample volume is cylindrical. The sample inlet opening, through which the liquid sample flows into the sample volume, as well as the sample outlet opening, through which the liquid sample flows out of the sample volume, are both provided at the vial head. According to the present invention, the sample inlet opening is not arranged at the top surface of the vial head, but is arranged at the cylindrical lateral surface of the vial head. The sample inlet opening is arranged axially closer to the sample vial than the sample outlet opening so that the inlet opening is arranged below the outlet opening if the sample vial and the vial head are standing vertically upright.

The inlet opening axis of the sample inlet opening is the spatial middle axis of the sample outlet duct, and is thereby identical with the current flow vector of the liquid flowing out of the sample inlet opening into the sample volume. The inlet opening axis is not orientated at a right angle with respect to the plane of the inlet opening because the inlet opening is tapered.

The inlet opening axis of the sample inlet opening is inclined with respect to the inlet cross plane with an inclination angle of 10° to 80°. The inlet cross plane is a plane arranged in a right angle with respect to the longitudinal axis defined by the sample volume cylinder. In other words, the sample inlet opening is orientated with a vertical component in the direction of the sample vial so that the flow vector of the liquid flowing into the sample volume has a vertical component.

The inlet opening axis is also angled with respect to the radius line of the cylinder with a tangency angle of more than 15° so that the flow vector of the liquid flowing into the sample volume has a tangency component, or is orientated exactly tangentially, which would correspond to a tangency angle of about 90°.

The liquid flowing into the sample volume therefore flows to the bottom of the sample vial in a helical line along the lateral inner surface of the sample volume. The flow impulse of the liquid is reflected backwards and is reduced at the bottom wall of the sample vial so that the liquid flows back in the direction of the vial head through the center region of the sample volume. The sample outlet opening is, as seen in the direction of the back-flowing liquid, arranged behind the sample inlet opening so that the liquid can expand radially outwardly behind the sample inlet opening without colliding with the liquid flowing into the sample volume through the sample inlet opening.

Experiments have shown that this arrangement of the sample inlet opening and the sample outlet opening allows a considerable decrease in the sample exchange interval to less than 20-30 seconds. The short sample exchange interval results in an increased measurement frequency, so that the reaction time is decreased, and the control quality of the control circuit is improved accordingly.

In an embodiment of the present invention, the vial head can, for example, be provided with a light-trap structure, and the sample inlet opening can, for example, be arranged axially beyond the light-trap structure. The light-trap structure is arranged opposite to the bottom wall of the sample vial. It can be advantageous if the measurement beam is directed axially through the vial bottom wall into the sample volume. The light-trap structure can generally be realized in many different ways. Many light-trap structures extend axially from the axial end of the vial head into the sample volume so that the fluidic cross sectional area is reduced by the light-trap structure. The back-flowing sample liquid can thereby be forced radially outwardly by the light-trap structure. Since the sample inlet opening is arranged axially beyond the light trap structure, i.e., with an axial distance to the light-trap structure, the back-flowing sample liquid current does not collide with the in-flowing sample liquid current.

In an embodiment of the present invention, the light-trap structure can, for example, be a conical light-trap body which extends axially from the axial end of the vial head. The conical angle of the light-trap body can, for example, be smaller than 45° with respect to the longitudinal axis. The sample inlet opening can, for example, be arranged axially beyond the tip of the conical light-trap body, as seen from the sample outlet opening.

The conical light-trap body is an efficient light-trap structure and also allows a laminar axial flow of the back-flowing sample liquid current along the light-trap cone. The steeper the cone is, the better is the light-trapping effect and the laminar flow quality of the liquid flowing along the cone.

In an embodiment of the present invention, the sample outlet opening can, for example, be arranged at the axial top end of the sample volume. If the light-trap structure is provided as a cone, the outlet opening is provided in the basic plane of the cone and adjacent to the cone basis. If no light-trap structure is provided and the axial end of the vial head is provided as a plane end wall, the sample outlet opening can be arranged in the middle of the end wall.

In an embodiment of the present invention, the inner surface of the vial head can, for example, be completely black and matt to improve the light-absorbing quality of the vial head.

In an embodiment of the present invention, the diameter of the cylindrical sample volume can, for example, be 5 mm to 30 mm, and, for example, be 10 mm to 20 mm, so that the diameter of the cylindrical sample volume is relatively small. Since the diameter of the cylindrical sample volume is relatively small, the total volume of the sample volume is reduced significantly. The sample exchange interval is thereby also reduced significantly.

In an embodiment of the present invention, the inclination angle of the inlet opening axis can, for example, be between 45° and 75°. The inclination angle can, for example, be chosen to cause a screw-like or helical sample current path down to the bottom wall of the sample vial with a rotational angle of at most 250° to 200° so that the inflowing sample current does not collide with itself. The rotational angle is affected by the longitudinal length of the vial and the inclination angle and is also slightly affected by the liquid current inlet speed.

In an embodiment of the present invention, the axial distance of the sample inlet opening to the bottom wall of the sample vial can, for example, be more than 30 mm and can, for example, be less than 150 mm. The axial distance should be as low as possible to avoid the helical sample current extending for a total rotational angle of more than 250° to 200° to avoid the inflowing sample current from colliding with itself.

An embodiment of the present invention is described below with reference to the drawings.

FIG. 1 shows a schematically a nephelometric process turbidimeter 10 for quasi-continuously measuring the turbidity of a liquid sample 19, for example, of drinking water.

The turbidimeter 10 is provided with a transparent and cylindrical sample vial 20 and a non-transparent vial head 30 closing the top opening of the sample vial 20. The vial head 30 and the sample vial 20 together enclose and define a cylindrical sample volume 18 which is completely filled with the liquid sample 19. The sample vial lateral surface 22 of the sample vial 20 and the vial head lateral surface 32 of the vial head 30 are both cylindrical and have the same diameter D20, D30 so that they together define the cylindrical sample volume 18 with a longitudinal sample volume axis 21, for example, being orientated vertically.

The sample vial 20, which is cup-shaped, is provided with a plane and transparent vial bottom wall 23 lying in a cross plane with respect to the longitudinal sample volume axis 21. A measurement light source 12 is arranged outside the sample vial 20 under the vial bottom wall 23. The measurement light source 12 generates a light beam 25 which is substantially axially directed through the vial bottom wall 23 into the liquid sample 19. The light beam 25 is scattered by particles of the liquid sample 19, and a part of the scattered light is collected and reflected by a ring prism 14 reflecting the scattered light to a light detector 16.

The vial head 30 is made out of black plastic and is provided with a matt black inside surface. At the axial end portion of the vial head 30, the vial head 30 is provided with a light-trap structure 34 which is defined by a conical light-trap body 36. The cone angle between the conical surface of the conical light-trap body 36 and the longitudinal sample volume axis 21 is 45° at the most, and can, for example, be less than 45°. The axial height H3 of the conical light-trap body 36 with respect to the axial end portion of the vial head 30 is about 15 mm.

The vial head 30 is provided with a sample inlet conduit 41 with a sample inlet opening 40 through which the liquid sample continuously flows into the cylindrical sample volume 18 and is provided with a sample outlet conduit 51 with a sample outlet opening 50 through which the liquid sample 19 flows out of the cylindrical sample volume 18. The sample inlet opening 40 is arranged at the vial head lateral surface 32 of the vial head 30, and the sample outlet opening is arranged at the axial top end of the cylindrical sample volume 18 and adjacent to the base of the conical light-trap body 36.

The sample inlet opening 40 is arranged axially beyond the light-trap structure 34 with a longitudinal opening offset H2 of 20 mm with respect to the axial end portion of the vial head 30. The longitudinal opening offset H2 is larger than the axial height H3 of the conical light-trap body 36 so that the sample inlet opening 40 is arranged with an axial distance from the sample outlet opening 50 and does not laterally overlap with the light-trap structure 34. In other words, the sample inlet opening 40 is arranged axially closer to the sample vial 20 then the sample outlet opening 50 and the cone tip.

Figure 3:
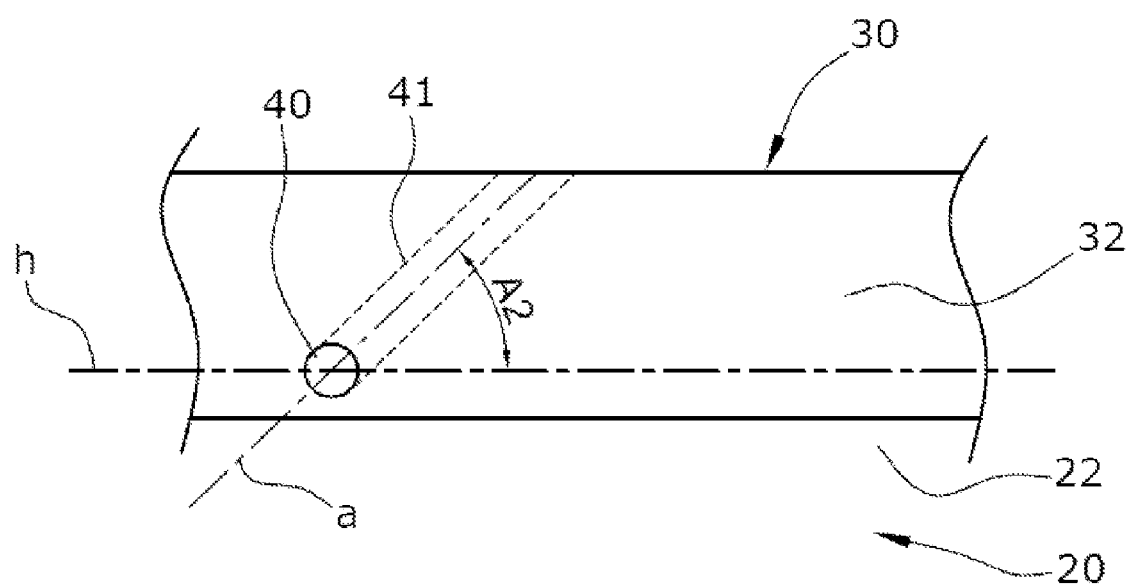
FIG. 3 shows the unfolded lateral surface of the vial head.

The orientation of the sample outlet opening axis is vertical so that the outlet current vector is orientated vertically. The sample inlet opening 40 is provided with an inlet opening axis a which is inclined with respect to the inlet cross plane h with an inclination angle A2 of about 60°, as only schematically shown in FIG. 3. The inlet opening axis a is additionally angled with respect to the radial line r of the vial head lateral surface 32 with a tangency angle A1 of more than 30°, for example, of more than 45°, and, for example, as close to 90° as possible.

The liquid sample 19 flows through the sample inlet opening 40 into the cylindrical sample volume 18 with a tangential flow vector which is directed downwardly so that the liquid current flows along the sample vial lateral surface 22 in a helical line with a total rotational angle of about 200° down to the vial bottom wall 23 where the liquid flow is reflected and decelerated so that the liquid flows back upwardly in a center column of the liquid sample 19. The liquid flow then arrives at the conical light trap body 36 and is thereby forced to flow radially outwardly, and finally leaves the cylindrical sample volume 18 via the sample outlet opening 50 and the sample outlet conduit 51.

The cylinder diameter D20, D30 of the sample vial lateral surface 22 and of the vial head lateral surface 32 is about 15 to 16 mm. The total axial length of the cylindrical sample volume 18 is about 80 mm so that the total volume of the cylindrical sample volume 18 is about 14000 mm$^3$.

The current speed of the inflowing liquid is highest so that the current speed of the liquid in all regions of the sample volume 18 is larger than the settling speed of a sand particle of, for example, 50 μm. A sand particle of 50 μm is therefore always carried away with the liquid current and cannot settle at the vial bottom wall 23 of the sample vial 20. The current speed of the inflowing liquid is adapted to allow the liquid to flow downwardly at the radial outside along the sample vial lateral surface 22 of the sample vial 20 and to flow upwardly in the center.

The present invention is not limited to embodiments described herein; reference should be had to the appended claims.

What is claimed is:

1. A nephelometric process turbidimeter for measuring a turbidity of a liquid sample, the nephelometric process turbidimeter comprising:

a sample vial configured to be transparent, the sample vial comprising a cylindrical sample vial lateral inner surface;

a vial head comprising a cylindrical vial head lateral inner surface, the vial head and the sample vial together defining a sample volume of a liquid sample having a shape of a cylinder;

a sample inlet opening comprising an inlet opening axis, the sample inlet opening being arranged at the vial head and being configured to have the liquid sample flow therethrough into the sample volume; and a sample outlet opening arranged at the cylindrical vial head lateral inner surface of the vial head to be axially closer to the sample vial than to the sample outlet opening, the sample outlet opening being configured to have the liquid sample flow therethrough out of the sample volume;

wherein, the inlet opening axis of the sample inlet opening is inclined with respect to a plane cutting across the sample inlet opening with an inclination angle of 10° to 80°, and is angled with respect to a radius line from a middle of the cylinder to the sample inlet opening with a tangency angle of more than 15°.

2. The nephelometric process turbidimeter as recited in claim 1, wherein the vial head further comprises a light-trap structure, and the sample inlet opening is arranged axially beyond the light-trap structure.

3. The nephelometric process turbidimeter as recited in claim 2, wherein the light trap structure is an axial conical light trap body.

4. The nephelometric process turbidimeter as recited in claim 1, wherein the sample outlet opening is arranged at an axial end of the sample volume.

5. The nephelometric process turbidimeter as recited in claim 1, wherein an inner surface of the vial head is black.

6. The nephelometric process turbidimeter as recited in claim 1, wherein a diameter of the cylinder is 5 to 30 mm.

7. The nephelometric process turbidimeter as recited in claim 1, wherein a diameter of the cylinder is 10 to 20 mm.

8. The nephelometric process turbidimeter as recited in claim 1, wherein the sample vial further comprises a bottom wall, and a distance of the sample inlet opening to the bottom wall is more than 30 mm.

9. The nephelometric process turbidimeter as recited in claim 1, wherein the inclination angle is between 45° and 75°.

* * * * *